United States Patent
Cooper, III et al.

[19]

[11] Patent Number: 6,108,403

[45] Date of Patent: Aug. 22, 2000

[54] X-RAY EQUALIZATION FILTER

[75] Inventors: Virgil N. Cooper, III, Sagamore Hills; Zhongmin Lin, Twinsburg, both of Ohio

[73] Assignee: Picker International, Inc., Cleveland, Ohio

[21] Appl. No.: 09/063,767

[22] Filed: Apr. 21, 1998

[51] Int. Cl.[7] .................................................. G21K 3/00
[52] U.S. Cl. ............................. 378/156; 378/159; 378/18
[58] Field of Search .................................... 378/156, 159, 378/18, 8

[56] References Cited

U.S. PATENT DOCUMENTS

| | | | |
|---|---|---|---|
| 3,755,672 | 8/1973 | Edholm et al. | 250/322 |
| 3,937,963 | 2/1976 | Hounsfield . | |
| 3,946,234 | 3/1976 | Hounsfield . | |
| 4,053,781 | 10/1977 | Hounsfield | 378/18 |
| 4,129,524 | 12/1978 | Nagai et al. . | |
| 4,182,821 | 1/1980 | Nagai et al. . | |
| 5,625,665 | 4/1997 | Fokkink et al. | 378/156 |

OTHER PUBLICATIONS

Material Safety Data Sheet for Oatey #95 Tinning Flux (Lead Free) having a date of issue of Sep. 19, 1997 and published by Oatey Corporation of Cleveland, OH.

Lam, Chan; "Effects of x-ray beam equalization on mammographic imaging"; Med. Phys. 17(2), Mar./Apr. 1990, pp. 242–249.

Product Data Sheets from Nuclear Associates of Carle Place, N.Y., pp. 120–125, 129, 131, 172.

*Primary Examiner*—David P. Porta
*Assistant Examiner*—Pamela R. Hobden
*Attorney, Agent, or Firm*—Timothy B. Gurin; John J. Fry; Eugene E. Clair

[57] ABSTRACT

An object (22) is positioned on a patient support (25) between an x-ray source (10) and an x-ray detector assembly (15). The x-ray source (10) is selectively activated to transmit an x-ray beam (20) through an imaging region (32) to the x-ray detector assembly (15). Positioning of the object (22) on the patient support (25) is such that a gap 33 exists in the imaging region (32) through which x-rays may pass unattenuated. An x-ray equalization filter (30) is introduced into the gap 33 and substantially conforms to its shape. The equalization filter (30) comprises a fluid medium disposed in a flexible receptacle. The fluid medium contains x-ray attenuating material suspended in a gel base. Placement of the equalization filter (30) in the gap reduces the number of unattenuated x-rays reaching the x-ray detector assembly (15) thereby enhancing image quality.

14 Claims, 3 Drawing Sheets

X-RAY EQUALIZATION FILTER

TECHNICAL FIELD

The present invention relates to the art of x-ray examinations. It finds particular application in conjunction with angiographic examinations of a patient's femur and lower extremities.

BACKGROUND OF THE INVENTION

X-ray systems are often used to perform angiographic examinations. Examples of x-ray systems suitable for such examinations include digital fluoroscopy, analog fluoroscopy, spot imaging and planar tomography. In such systems, an x-ray source is disposed on one side of a patient and an x-ray detector is disposed on the other side. The x-ray detector converts x-rays which have passed through the patient into secondary carriers (i.e. visible light) which are converted to a video signal. Because blood is relatively transparent to x-rays, the patient is injected with a radiopaque dye which has relatively good x-ray absorption such that blood vessels are more conspicuous in a resultant image. Images of a circulatory system may then be obtained by subtracting a processed reference or basis image taken before injection of the dye from a processed image taken after injection of the dye.

One application of x-ray angiography is imaging blood flow in a patient's lower extremities. The radiopaque dye is introduced into an artery in the pelvic or lower abdomen area and flows with the blood down the patient's leg. The dye is then imaged as it flows down the leg. Such a procedure is often referred to as an angiographic femoral runoff. In a normal healthy patient with good circulation, the dye moves from the pelvic area to the toes fairly quickly, whereas in a patient with artery blockage the dye may take a significantly longer time to reach the toes or may not reach there altogether. Thus, by virtue of examining the distal most conspicuous portion of the artery or vessel injected with the dye, areas of possible artery blockage may be inferred.

During x-ray imaging, an intensity level of x-rays reaching the x-ray detector is monitored to assure that the overall intensity of x-rays received by the x-ray detector is satisfactory to produce an image of diagnostic quality. The intensity of the x-rays received by the x-ray detector is measured in terms of exposure. If it is determined that the x-ray detector is not receiving a satisfactory exposure to x-rays, a signal is sent to the x-ray source to increase either one, or both, of the number of x-rays produced and/or the energy of the x-rays.

One difficulty associated with producing angiographic and other x-ray images is that x-rays incident on the x-ray detector are either of an intensity level which is too high or too low thereby resulting in reduced image quality. Take, for example, a situation in which a patient is lying horizontally on a patient support having an x-ray source disposed below the patient which transmits x-rays to an x-ray detector positioned above the patient. An imaging region as seen by the x-ray detector will often include regions representative of gaps between the patient's anatomy as commonly exist, for example, between the patient's legs in an angiographic femoral runoff examination. Such gaps allow unattenuated x-rays to reach the x-ray detector. Unfortunately, the high exposure associated with unattenuated x-rays cause the x-ray detector to prematurely believe that it is satisfied with the overall intensity level of the incident x-rays when, in fact, the intensity level of the x-rays passing thought the patient's anatomy may be below that needed to obtain a high quality image. As a result, the portion of the x-ray detector corresponding to the anatomy of interest is often underexposed to x-rays.

Another difficulty associated with having gaps in the imaging region through which x-rays may pass unattenuated, relates to gray scale mapping which occurs prior to image display on a monitor. More specifically, image quality is substantially based on the ability to see contrast between certain types of anatomy on the monitor. Therefore, the range of energy levels as accumulated by each pixel of the x-ray detector during an exposure is mapped to a gray scale consisting of, for example, 256 steps from black to white. Detected x-rays which are mapped into a central portion of the 256 steps will typically provide sufficient contrast to readily distinguish among different anatomy whereas images mapped near the upper or lower extremities of the gray scale will typically fail to exhibit enough image contrast to properly distinguish and interpret such portions of the image. Unfortunately, x-rays which reach the detector with little to no attenuation through gaps in the patients anatomy will typically cause mapping of the final image to be skewed such that the area of relevant anatomy is mapped to an extreme of the gray scale where there in not enough image contrast to distinguish between relevant anatomy. This occurs since the detector pixels receiving the unattenuated x-rays cause there to be a wide dynamic range of energies to be mapped in most of the gray scale steps (i.e. 256 steps) thereby causing the range of energies holding the relevant image data to be mapped to region having lower overall gray scale contrast.

One known way to reduce the effect of unattenuated x-rays as seen by an x-ray detector is to introduce aluminum bars in the gaps between the patient's anatomy. Such aluminum bars are typically sized and shaped to provide x-ray attenuation similar to the attenuation of an x-ray beam passing through a patient's body. For instance, the aluminum bars may be approximately one inch thick and several inches long. By placing one or more of the aluminum bars in the gaps between the patient anatomy in the imaging region, the number of unattenuated x-rays reaching the x-ray detector is reduced. Unfortunately, the rigidity of the aluminum bars makes it difficult to completely block all unattenuated x-rays from reaching the x-ray detector as the bars do not conform to curves and other shapes which may exist with respect to the patient's anatomy. Thus, the mapping of the x-ray energies received by the x-ray detector to a gray scale will still often result in pertinent anatomy being mapped to a region having insufficient contrast since some unattenuated x-rays often still bombard the x-ray detector thereby skewing the mapping as discussed above.

Another device for reducing the effect of unattenuated x-ray reaching the x-ray detector is to use a compensation filter which is specifically designed for a region of interest to be imaged. Compensation filters are typically a rigid lead-plastic filter which is placed on top of the anatomy of interest and is specially sized and shaped to reduce the large dynamic range of energies which are incident upon the x-ray detector. Compensation filters of this type are commercially available from Nuclear Associates of Carle Place, New York. Unfortunately, because compensation filters are typically designed for imaging of a specific region having generally known attenuation characteristics, such compensation filters are not often suitable when imaging other anatomy which may have varying sized and shaped gaps in the imaging region.

Another difficulty associated with x-ray angiographic imaging techniques is that real time images may become blurred by virtue of movement by a patient during the imaging procedure. To reduce such movement, patients may at times be strapped or otherwise secured to the patient support however such physical constraints are often discomforting to the patient and, depending on the material of the constraint used, could lead to the introduction of artifacts in the resultant image. If patient supports are not used then, of course, there is a greater possibility that the patient may move thereby blurring the final image.

Therefore, what is needed is a method and apparatus which overcomes the shortfalls discussed above and others.

SUMMARY OF THE INVENTION

In accordance with the present invention, an x-ray equalization filter is provided. The equalization filter consists of a fluid medium disposed in a flexible receptacle. The fluid medium is comprised of materials which allow the equalization filter to readily conform to various shapes so that it may be used to completely fill gaps existing between a patient's anatomy in an imaging region. The fluid medium includes a gel like base having x-ray attenuating material suspended therein. The x-ray attenuating material includes elements having a high atomic number so as to provide sufficient attenuation of x-rays passing through the equalization filter. For instance, the attenuation may be such as to approximate the amount of attenuation which typically occurs as x-rays pass through a portion of anatomy being imaged. The flexible receptacle provides a means for containing the fluid medium and is made of a material which is resistant to punctures, easy to seal, easy to clean and is reusable.

During x-ray imaging the equalization filter is placed in gaps which exist between a patient's anatomy in an imaging region. When placed in such gaps, the equalization filter contours to the shape of the gap thereby significantly reducing the probability that space exists through which x-rays may pass unattenuated to the x-ray detector. By virtue of selecting an appropriate sized flexible receptacle having an appropriate amount fluid medium, the equalization filter is able to attenuate x-rays incident on it to a desired amount before reaching the x-ray detector. In this manner, the x-ray intensity level reaching the x-ray detector is more uniform and predictable, thereby providing a greater assurance that gray scale mapping will cause the relevant image to be mapped to region having sufficient contrast. Also, placement of one or more equalization filters in gaps or abutting an outer periphery of a patient's anatomy increases patient stabilization thereby reducing image blurring which may otherwise occur due to movement of the patient during imaging.

According to one aspect of the present invention a method of reducing unattenuated x-rays from reaching the x-ray detector is provided. The method includes the step of positioning an object between an x-ray source and the x-ray detector, the object defining a gap through which x-rays may pass to the x-ray source unattenuated. An equalization filter is positioned within the gap and is able to substantially form to a shape of the gap. An x-ray detector receives the x-ray beam, a portion of which contains x-rays attenuated by the object and another portion of which contains x-rays attenuated by the equalization filter. Based on the information contained in the x-ray beam, an image of the object is reconstructed.

In accordance with yet another aspect of the present invention a method of generating a diagnostic image of a patient is provided. The method includes the steps of positioning the patient in an imaging region of an x-ray apparatus, the patient covering a first portion of the imaging region, placing an equalization filter in a second portion of the imaging region, the equalization filter capable of conforming to various shapes, directing an x-ray beam through the imaging region and receiving the x-ray beam and reconstructing a human readable image.

In accordance with another aspect of the present invention, a device for use with an x-ray imaging apparatus is provided. The device including a flexible receptacle, and a fluid medium disposed in the flexible receptacle. The fluid medium includes a gel base and an x-ray attenuating material suspended in the gel base.

In accordance with a more limited aspect of the present invention, the x-ray attenuating material includes one or more elements having an atomic number greater than twelve such as tin, copper and bismuth.

One advantage of the present invention is that the equalization filter is able to conform to varying body shapes thereby allowing the equalization filter to completely fill any gaps between a patient's anatomy.

Another advantage of the present invention is that the fluid medium within the equalization filter includes elements having a high atomic number thereby allowing the equalization filter to remain a manageable size yet still attenuate x-rays to a desirable degree so as to obtain readable images.

Yet another advantage of the present invention is that it functions to help stabilize a patient during x-ray imaging so as to reduce image blurring cause from patient movement.

Still another advantage of the present invention is that it the equalization filter is inexpensive to produce.

To the accomplishment of the foregoing and related ends, the invention then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE PREFERRED EMBODIMENTS

Figure 1:
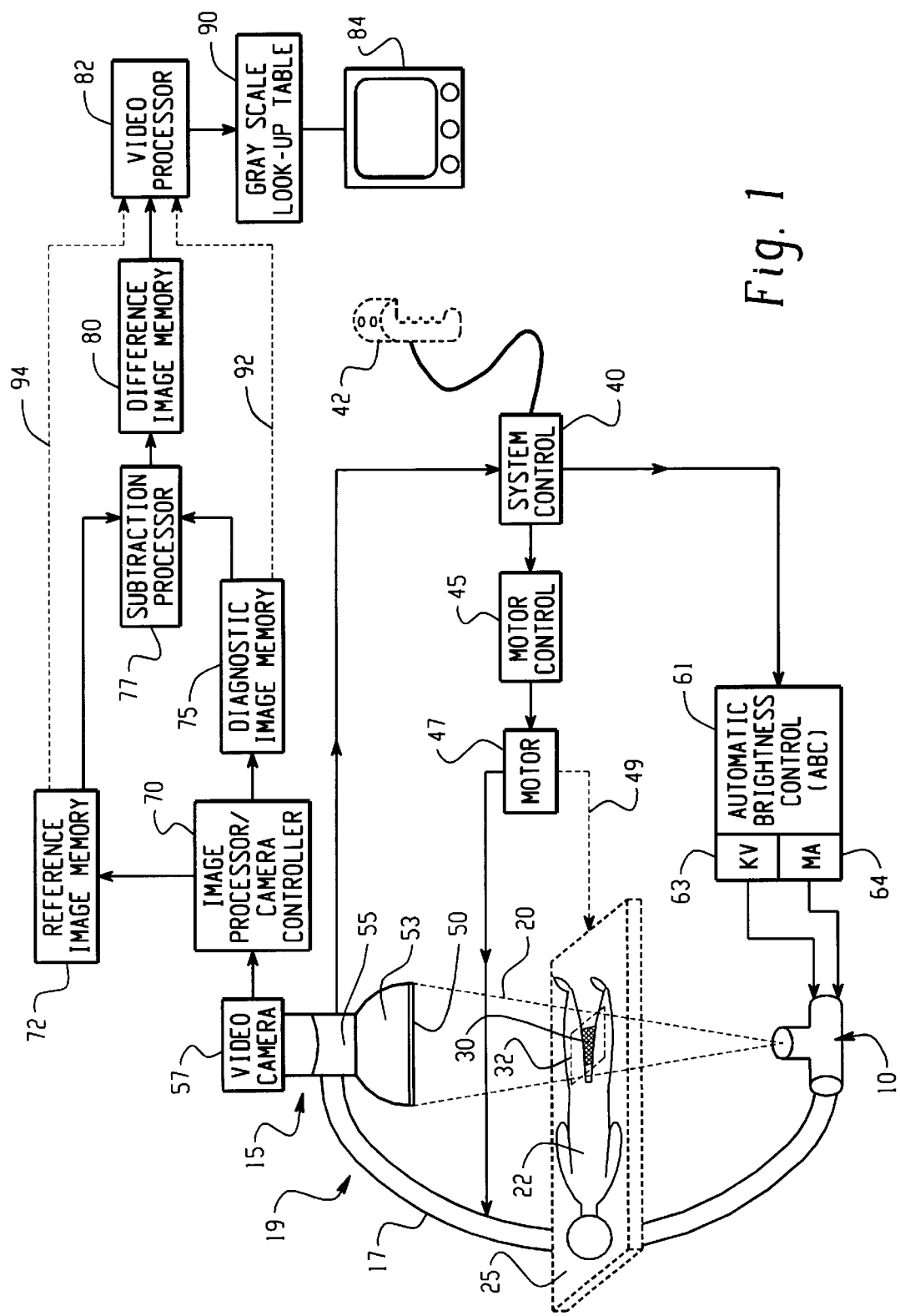
FIG. 1 is a diagrammatic illustration of a digital angiographic system in accordance with the present invention.

The present invention will now be described with reference to the drawings in which like reference numerals are used to refer to like elements throughout.

Turning now to FIG. 1, an x-ray source 10 such as an x-ray tube is coupled to an x-ray detector assembly 15 via a C-arm 17. The combination of the X-ray source 10, the x-ray detector assembly 13 and C-arm 17 shall hereinafter be collectively referred to as C-arm assembly 19. The x-ray source 10 selectively passes an x-ray beam 20 through an object or patient 22 supported by a patient support 25 to the x-ray detector assembly 15 for imaging of the patient 22. In the present embodiment, an x-ray equalization filter 30 is disposed in an imaging region 32 so as to reduce the number of unattenuated x-rays reaching the x-ray detector assembly 15 as discussed in more detail below. More specifically, the equalization filter 30 is disposed in a gap 33 in the imaging region defined by the patient's anatomy.

Continuing to refer to FIG. 1, a system control 40 controls movement of the C-arm assembly 19 relative to the patient support 25. The system control 40 may be preprogrammed with a specified protocol for moving the C-arm assembly 19 with respect to the patient support 25 or may provided with movement instructions by an operator through hand-held unit 42. A motor control unit 45 receives movement commands from the system control 40 and activates motor 47. In the present embodiment, the motor 47 is coupled to the C-arm assembly 19 thereby providing for movement of the C-arm assembly 19 in a direction parallel to a longitudinal axis of the patient support 25. It will be appreciated, however, that in an alternative embodiment, the motor 47 could be coupled directly to the patient support 25 as depicted by dashed line 49 thereby providing movement to the patient support 25 while the C-arm assembly 19 remains stationary.

The x-ray detector assembly 15 includes a phosphor plate or sheet 50 disposed behind an optically opaque but radiation transparent shield. The phosphor converts received radiation into a faint optical image. The phosphor plate 50 is part of an image intensifier 53 that boosts the intensity of the optical image. A lens system 55 focuses the intensified optical image onto an image pick-up surface of a video camera 57. Preferably, the video camera 57 is a digital video camera that produces digital video signals. The video camera 57 is held at a ready to acquire image state and starts to produce images in response to an external signal as is conventionally in the art. Alternatively, other opto-electrical converters may be utilized to convert the optical image into an electronic image representation. Further, it will be appreciated that other x-ray direct photo-conductor detectors could be used in place of the phosphor plate as is known in the art.

The system control 40 couples an output from the image intensifier 53 to an automatic brightness control unit (ABC unit) 61 so as to allow for varying of the x-ray beam intensity level as is discussed in more detail below. The ABC unit 61 is coupled to the x-ray detector 10 and serves to control the intensity level of the x-ray beam 20 transmitted from the x-ray source 10. More specifically, the ABC unit 61 provides both a kilo-volt signal 63 and a milli-amp signal 64 to the x-ray source 10. The kilo-volt signal 63 serves to vary the energy level of the x-rays produced while the milli-amp signal 64 serves to vary the amount of x-rays produced and emitted by the x-ray source 10 per unit time.

The video camera 57 is coupled to an image processor/camera controller 70 which stores image data into either reference image memory 72 or diagnostic image memory 75 depending on the type of image being processed. For instance, when acquiring images of the patient 22 prior to injection of a radiopaque dye, such images are stored in the reference image memory 72. Following injection of the radiopaque dye, the image processor/camera controller 70 stores the images into the diagnostic image memory 75. The reference image memory 72 and the diagnostic image memory 75 are coupled to a image subtraction processor 77. The image subtraction processor 77 serves to subtract a reference image for a particular position from each of the diagnostic images for the same location and loads the generated difference images in a difference image memory 80. A video processor 82 is coupled to the difference image memory 80 and serves to convert the difference image into a format suitable for display on video monitor 84. More specifically, upon receiving a difference image, the video processor 82 utilizes a gray scale look-up table 90 to map the accumulated x-ray energy associated with each image pixel with an appropriate gray scale brightness level so as to display the full spectrum of x-ray energy levels detected by the image intensifier 53. Alternatively, rather than displaying the difference image, the diagnostic images and/or reference images may be conveyed directly to the video processor 82 for display as represented by dashed lines 92 and 94 respectively. For example, as diagnostic images containing radiopaque dye are often sufficiently distinctive that the dye's progress through the blood vessels is readily apparent even when the surrounding tissue and bones are displayed, such images may be passed directly from the diagnostic image memory 75 to the video processor 82 for viewing.

Figure 2:
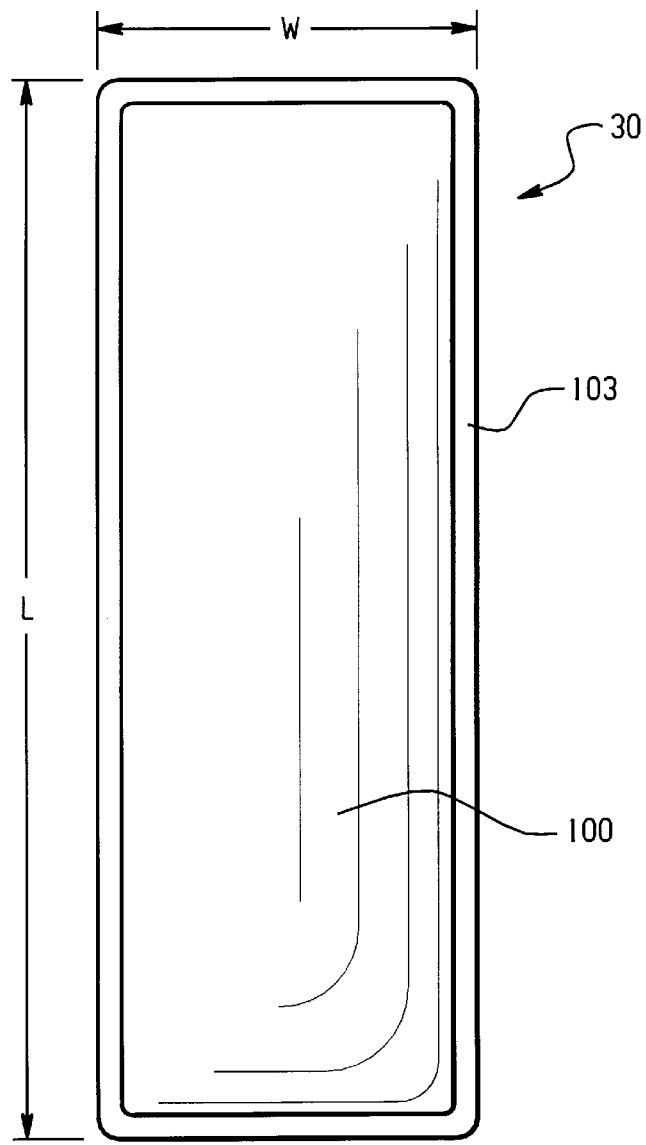
FIG. 2 is a top plan view of the x-ray equalization filter of the present invention.
Figure 3:
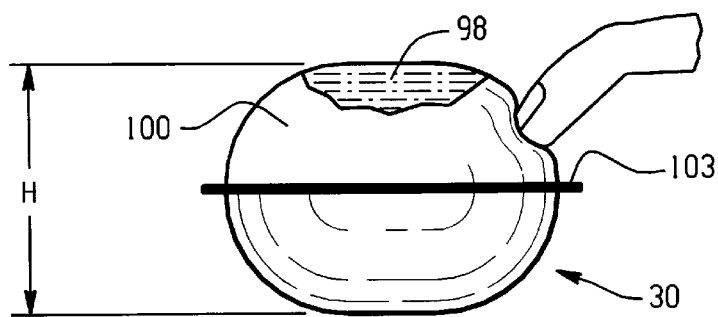
FIG. 3 is a side plan view showing of the equalization filter of FIG. 2.
Figure 5:
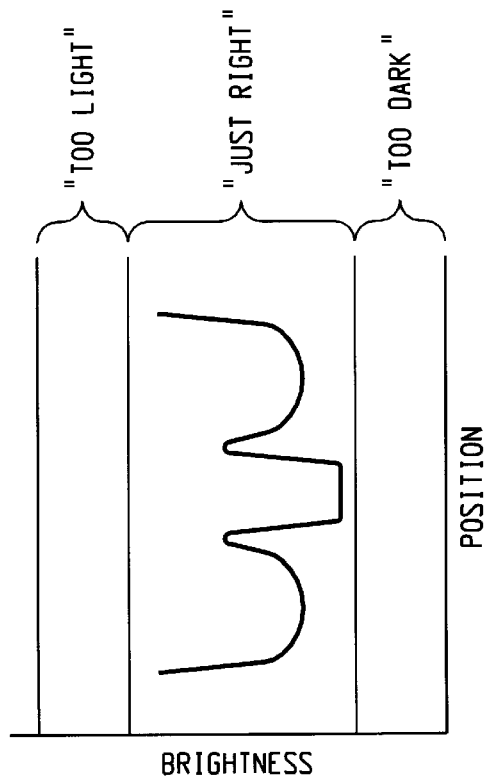
FIG. 5 is a brightness diagram representative of the mapping of the x-ray intensity profile of FIG. 4 to a gray scale for display on a monitor.

Referring now to FIGS. 2 and 3, the equalization filter 30 of the present embodiment is shown in more detail. The equalization filter 30 is shown to include a fluid medium 98 disposed in a flexible receptacle 100. The flexible receptacle 100 of the present embodiment is made of a ten (10) oz/square-yard vinyl. Vinyl is utilized in the preferred embodiment as it is puncture resistant, easy to clean and conforms well to various shapes. Further, vinyl is easy to seal. In the present invention, the receptacle 100 is sealed along its peripheral edge 103 using conventional thermal sealing techniques known for vinyl. It will be appreciated that various other flexible plastics and other material may also be used for the receptacle 100 and the present invention is not limited to any specific material.

The fluid medium 98 of the present embodiment is composed of a gel base which is capable of suspending a predetermined amount of x-ray attenuating material. The amount of x-ray attenuating material to be suspended depends on the atomic number of the x-ray attenuating material(s) utilized. In the present invention, the x-ray attenuating materials used will preferably have a high atomic number. As is known in the art, the x-ray attenuating characteristics of a given element is generally proportional to the atomic number of the element taken to the fourth power for photoelectric interactions. For purposes of the present invention, materials having a high atomic number are considered to be those materials having an effective atomic number of twelve (12) or greater. The present invention has found that materials having such high atomic numbers provide sufficient x-ray attenuating characteristics when suspended in a gel base to allow the overall size and thickness of the equalization filter 30 to be reasonable with respect to the patient size. The amount of x-ray attenuation provided for in a given equalization filter 30 will vary depending on the imaging region and use contemplated, however, in the present embodiment the attenuation is substantially equal to the amount of attenuation expected through a patient's thigh. More specifically, the equalization filter 30 of the present embodiment is sized for use in angiographic femoral runoff examinations and has the dimensions of a two (2) inch Height H, six (6) inch width W, and eighteen (18) inch length L. It will be appreciated, however, that the equalization filter 30 may take on a variety of other sizes and shapes depending on the particular use intended. In the present embodiment, the following concentration of x-ray attenuating materials are included in the fluid medium 98 in the amounts indicated: Tin (4–8%); Copper (less than 1%), and Bismuth (less than 1%). Of course, varying concentrations of any of these elements may be used alone or in combination with other x-ray attenuating material. Additionally, a variety of other x-ray attenuating materials and combinations of materials could alternative be used.

The gel base of the fluid medium 98 is composed of material which can readily conform to various shapes while maintaining a uniform consistency of the x-ray attenuating material throughout the fluid medium 98. In the present embodiment, the following materials are included as part of the gel base of the fluid medium 98 in the amounts indicated: Zinc Chloride (10–20%); Ammonium Chloride (1–4%); and Petrolatum (65–80%). It will be appreciated, however, that other materials capable of suspending the x-ray attenuating material may alternatively be used.

A fluid medium 98 suitable for use with the present invention and having the characteristics described above with respect to the x-ray attenuating materials and the gel base is commercially available under the name Oatey #95 tinning flux (lead free)from Oatey Corporation of Cleveland, Ohio. A Material Safety Data Sheet for Oatey #95 Tinning Flux (lead free) having a date of issue of Sep. 19, 1997 is published by Oatey Corporation and is hereby incorporated by reference.

In operation, the equalization filter 30 of the present invention is provided in gaps between a patient's anatomy in the imaging region 32 as shown in FIG. 1. Given its flexible properties, the equalization filter 30 is able to readily contour, or form, to the shape of the gap and completely fill all areas through which x-rays would otherwise pass unattenuated. Once the equalization filter 30 is properly situated in the gap, the system control 40 activates the x-ray source 10 for imaging of the patient. The ABC unit 61 initially sets the x-ray beam 20 to a default intensity level. During an exposure, the image intensifier 53 determines whether the intensity of the incident x-ray beam 20 is sufficient to obtain a readable image. If the intensity level of the incident x-ray beam 20 is too high or too low, the ABC unit 61 sends a signal to the system controller 40 indicating that the intensity level needs to be adjusted. In response, either one, or both, of the kilo-volts 63 and/or the milli-amps 64 applied to the x-ray source 10 are adjusted. When imaging a patient 22 without the equalization filter 30, unattenuated x-rays passing through gaps often cause the intensity of x-rays incident on the image intensifier 53 to be higher than would be expected without such gaps. As such, the image intensifier 53 would send signals back to the ABC unit 61 often causing the x-ray source 10 to under expose the patient to x-rays as discussed above in the background section. When imaging a patient 22 with the equalization filter 30, however, there is a more uniform distribution of x-ray intensities presented to the image intensifier 53 given the ability of the equalization filter 30 to conform to various shapes. As such, the image intensifier 53 more accurately adjusts the x-ray intensity level since the measured intensity level at the image intensifier 53 is not erroneously satisfied by unattenuated x-rays. Further, there will likely be a much narrower dynamic range of x-ray energies to be mapped to a gray scale since high energy unattenuated x-rays are not bombarding the x-ray detector assembly 15 thereby allowing for more readable image qualities as discussed below. It will be noted that it is also not preferable that the equalization filter 30 completely block all x-rays since this may erroneously lead to over exposure of x-rays to the patient 22.

Figure 4:
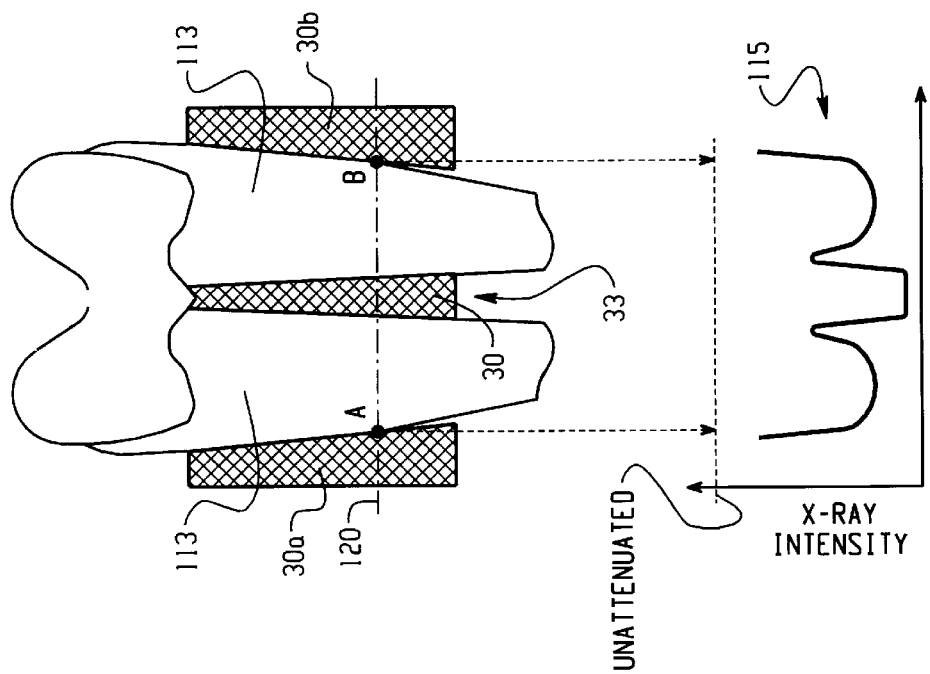
FIG. 4 is a diagrammatic representation of the equalization filter of the present invention placed between the thighs of a patient and a resulting x-ray intensity profile taken across a particular cross-section.

Referring now to FIG. 4, an equalization filter 30 is shown situated between a patient's thighs 113 during an angiographic femoral runoff examination. Also shown is x-ray intensity profile graph 115 taken between points A and B along profile line 120. Because the equalization filter 30 is able to conform to, and completely fill, the gap 33 between the patient's thighs 113 in this example, there is a substantial reduction in the number of unattenuated x-rays which pass to the image intensifier 53. As such, when the image from the intensity profile graph 115 is mapped to the 256 gray scale by the video processor 82 as discussed above, it has a sufficiently narrow dynamic range to preserve contrast in the region of interest. If, however, the x-rays were totally unattenuated at the image intensifier 53, then the imaging region might have too wide of a dynamic range to be mapped in the 256 gray scale while preserving contrast in the region of interest. Since, however, the present invention provides a way to significantly decrease the likelihood that a large portion of unattenuated x-rays reach the image intensifier 53 there is an increased likelihood that each image will be of readable quality thereby saving time for a physician and reducing the amount of x-ray dose ultimately applied to a patient.

Referring again to FIG. 4, an additional use for the equalization filters 30 is depicted. More specifically, a pair of equalization filters 30a, 30b are shown to be positioned about the outer regions of the patient's thighs to help stabilize the patient so he or she does not move during the imaging procedure. In the event the imaging region is wider than that shown between points A and B, the equalization filters 30a, 30b would also be useful in attenuating x-rays which may otherwise pass unattenuated to the image intensifier 53. Given the size and weight of the equalization filters 30 as described with respect to the preferred embodiment, such equalization filters 30 serve to stabilize the patient thereby ultimately reducing blurring caused by patient movement. Although it is shown that two equalization filters 30a, 30b are utilized to provide patient stabilization, it will be appreciated that any number of equalization filters may independently be positioned for the same purpose.

The invention has been described with reference to the preferred embodiments. Obviously, modifications and alterations will occur to others upon reading and understanding the preceding detailed description. It is intended that the invention be construed as including all such modifications, alterations and others insofar as they come within the scope of the appended claims or their equivalence thereof.

What is claimed is:

1. A method of generating a diagnostic image of an object comprising the steps of:

positioning the object in an imaging region of an x-ray apparatus, the object covering a first portion of the imaging region;

placing an equalization filter in a second portion of the imaging region, the equalization filter capable of conforming to various shapes, the equalization filter approximating the total attenuation of x-rays for the portion of the object being imaged;

directing an x-ray beam from an x-ray source through the imaging region;

receiving the x-ray beam and reconstructing a human readable image; and controlling the x-ray source in response to the received x-ray beam.

2. The method of claim 1, wherein the equalization filter is comprised of a fluid medium disposed in a flexible receptacle.

3. The method of claim 2, wherein the fluid medium includes an x-ray attenuating material having a high atomic number greater than or equal to 12.

4. The method of claim 3, wherein the x-ray attenuating material includes at least one of tin, copper, and bismuth.

5. The method of claim 4, wherein the fluid medium includes 3–5 percent by concentration of tin, less than 1 percent by concentration of copper and, less than 1 percent by concentration of bismuth.

6. The method of claim 2 wherein the flexible receptacle is comprised of vinyl.

7. The method of claim 6, wherein the flexible receptacle is thermally sealed.

8. An equalization filter having an approximate total attenuation of x-rays similar to a total attenuation of x-rays for a portion of an object to be imaged, the equalization filter comprising:

a sealed flexible receptacle; and a fluid medium disposed in the flexible receptacle; wherein the volume of fluid medium within the receptacle includes a gel base and a predetermined amount of x-ray attenuating material suspended in the gel base to approximate the total attenuation of x-rays for the portion of the object being imaged.

9. The filter of claim 8, wherein the x-ray attenuating material includes one or more elements having an atomic number greater than or equal to twelve.

10. The filter of claim 9 wherein the x-ray attenuating material includes at least one of tin, copper, and bismuth.

11. The filter of claim 10, wherein the fluid medium includes 3–5 percent by concentration of tin, less than 1 percent by concentration of copper and, less than 1 percent by concentration of bismuth.

12. The filter of claim 8, wherein the gel base is at least in part comprised of petrolatum.

13. The filter of claim 8, wherein the flexible receptacle is comprised of vinyl.

14. The filter of claim 8, wherein the flexible receptacle is thermally sealed.

* * * * *